(12) United States Patent
Gobron et al.

(10) Patent No.: US 10,136,980 B2
(45) Date of Patent: Nov. 27, 2018

(54) IMPLANTS AND PROCEDURES FOR SUPPORTING ANATOMICAL STRUCTURES FOR TREATING CONDITIONS SUCH AS PELVIC ORGAN PROLAPSE

(71) Applicant: Caldera Medical, Inc., Agoura Hills, CA (US)

(72) Inventors: Stéphane Gobron, Thousand Oaks, CA (US); Anand Vemuri, Thousand Oaks, CA (US)

(73) Assignee: Caldera Medical, Inc., Agoura Hills, CA (US)

(*) Notice: Subject to any disclaimer, the term of this patent is extended or adjusted under 35 U.S.C. 154(b) by 51 days.

(21) Appl. No.: 15/136,616

(22) Filed: Apr. 22, 2016

(65) Prior Publication Data

US 2016/0235514 A1 Aug. 18, 2016

Related U.S. Application Data

(60) Continuation of application No. 14/286,953, filed on May 23, 2014, now abandoned, which is a division of
(Continued)

(51) Int. Cl.
*A61F 2/00* (2006.01)
*A61B 17/04* (2006.01)
(Continued)

(52) U.S. Cl.
CPC ........ *A61F 2/0045* (2013.01); *A61B 17/0401* (2013.01); *A61F 2/0063* (2013.01);
(Continued)

(58) Field of Classification Search
CPC .................. A61F 2/0045; A61F 2/0063; A61F 2220/0083; A61F 2220/0016; A61F 2220/0008; A61B 17/0401; A61B 17/06109; A61B 2017/0414; A61B 2017/0427; A61B 2017/0464;
(Continued)

(56) References Cited

U.S. PATENT DOCUMENTS 5,333,624 A 8/1994 Tovey
6,039,686 A 3/2000 Kovac
(Continued)

FOREIGN PATENT DOCUMENTS

WO WO 2008057261 A2 * 5/2008 ......... A61B 17/0401

OTHER PUBLICATIONS

United States Patent and Trademark Office, Office Action dated Apr. 23, 2015 in U.S. Appl. No. 14/286,953, 13 pages.
(Continued)

*Primary Examiner* — Kaylee Wilson
(74) *Attorney, Agent, or Firm* — Inskeep IP Group, Inc.

(57) ABSTRACT

Implants for the treatment of pelvic support conditions and methods of implementing the same. The implants comprise relatively soft, flexible bodies and relatively strong arms extending in predetermined orientations therefrom. Methods and devices for placing the implants minimize trauma to the pelvic floor and provide well-anchored support to pelvic organs without interfering with sexual or other bodily functions.

15 Claims, 20 Drawing Sheets

Related U.S. Application Data application No. 12/652,664, filed on Jan. 5, 2010, now Pat. No. 8,758,220.

(60) Provisional application No. 61/142,604, filed on Jan. 5, 2009.

(51) Int. Cl.
*A61B 17/06* (2006.01)
*A61B 17/00* (2006.01)

(52) U.S. Cl.
CPC .......... *A61B 17/06109* (2013.01); *A61B 2017/00805* (2013.01); *A61B 2017/0409* (2013.01); *A61B 2017/0412* (2013.01); *A61B 2017/0414* (2013.01); *A61B 2017/0427* (2013.01); *A61B 2017/0456* (2013.01); *A61B 2017/0464* (2013.01); *A61F 2220/0008* (2013.01); *A61F 2220/0016* (2013.01); *A61F 2220/0083* (2013.01)

(58) Field of Classification Search
CPC .. A61B 2017/00805; A61B 2017/0409; A61B 2017/0412; A61B 2017/0456
See application file for complete search history.

(56) References Cited

U.S. PATENT DOCUMENTS

| | | | |
|---|---|---|---|
| 6,595,911 B2 | 7/2003 | Lovuolo | |
| 6,652,450 B2 | 11/2003 | Neisz et al. | |
| 6,960,160 B2 | 11/2005 | Browning | |
| 7,131,944 B2 | 11/2006 | Jacquetin | |
| 7,229,404 B2 | 6/2007 | Bouffier | |
| 7,352,197 B1 | 4/2008 | Montpetit et al. | |
| 7,371,245 B2 | 5/2008 | Evans et al. | |
| 7,393,320 B2 | 7/2008 | Montpetit et al. | |
| 7,494,495 B2 | 2/2009 | Delorme et al. | |
| 7,500,945 B2 | 3/2009 | Cox et al. | |
| 7,524,281 B2 | 4/2009 | Chu et al. | |
| 7,527,588 B2 | 5/2009 | Zaddem et al. | |
| 7,527,633 B2 | 5/2009 | Rioux | |
| 7,645,286 B2 | 1/2010 | Catanese, III et al. | |
| 2004/0122474 A1 | 6/2004 | Gellman et al. | |
| 2005/0004424 A1 | 1/2005 | Raz et al. | |
| 2005/0004576 A1 | 1/2005 | Benderev | |
| 2005/0171563 A1 | 8/2005 | Heinrich et al. | |
| 2005/0250977 A1 | 11/2005 | Montpetit et al. | |
| 2005/0256530 A1* | 11/2005 | Petros ............... | A61B 17/0401 606/151 |
| 2005/0261547 A1 | 11/2005 | Bouffier | |
| 2006/0089525 A1 | 4/2006 | Mamo et al. | |
| 2006/0130848 A1 | 6/2006 | Carey | |
| 2006/0229493 A1 | 10/2006 | Weiser et al. | |
| 2006/0229596 A1 | 10/2006 | Weiser et al. | |
| 2006/0260618 A1 | 11/2006 | Hodroff et al. | |
| 2006/0265042 A1 | 11/2006 | Catanese, III et al. | |
| 2007/0021649 A1 | 1/2007 | Nowlin et al. | |
| 2007/0043255 A1 | 2/2007 | O'Donnell | |
| 2007/0055095 A1 | 3/2007 | Chu et al. | |
| 2007/0156175 A1 | 7/2007 | Weadock et al. | |
| 2007/0161849 A1 | 7/2007 | Goldberg | |
| 2007/0161850 A1 | 7/2007 | Harari et al. | |
| 2007/0162120 A1 | 7/2007 | Bouffier | |
| 2007/0173864 A1 | 7/2007 | Chu | |
| 2007/0270890 A1 | 11/2007 | Miller | |
| 2007/0299299 A1 | 12/2007 | Rosenblatt | |
| 2008/0004487 A1 | 1/2008 | Haverfield | |
| 2008/0004490 A1 | 1/2008 | Bosley, Jr. et al. | |
| 2008/0021265 A1 | 1/2008 | Garbin et al. | |
| 2008/0027271 A1 | 1/2008 | Maccarone | |
| 2008/0033232 A1 | 2/2008 | Catanese, III et al. | |
| 2008/0033488 A1 | 2/2008 | Catanese, III et al. | |
| 2008/0039874 A1 | 2/2008 | Catanese, III et al. | |
| 2008/0039894 A1 | 2/2008 | Catanese, III et al. | |
| 2008/0081945 A1 | 4/2008 | Toso et al. | |
| 2008/0082105 A1 | 4/2008 | Chu | |
| 2008/0082121 A1 | 4/2008 | Chu | |
| 2008/0097329 A1 | 4/2008 | Hodroff et al. | |
| 2008/0132753 A1 | 6/2008 | Goddard | |
| 2008/0140218 A1 | 6/2008 | Staskin et al. | |
| 2008/0161837 A1 | 7/2008 | Toso et al. | |
| 2008/0183031 A1 | 7/2008 | Montpetit et al. | |
| 2008/0196729 A1 | 8/2008 | Browning | |
| 2008/0208251 A1 | 8/2008 | Weadock et al. | |
| 2008/0287956 A1 | 11/2008 | Smith et al. | |
| 2008/0287968 A1 | 11/2008 | Smith et al. | |
| 2009/0005633 A9 | 1/2009 | Montpetit et al. | |
| 2009/0018387 A1 | 1/2009 | Veronikis | |
| 2009/0023982 A1 | 1/2009 | Karram | |
| 2009/0105526 A1 | 4/2009 | Piroli Torelli et al. | |
| 2009/0149700 A1 | 6/2009 | Garcia et al. | |
| 2009/0156891 A1 | 6/2009 | Heys et al. | |
| 2009/0171139 A1 | 7/2009 | Chu | |
| 2009/0171140 A1 | 7/2009 | Chu | |
| 2009/0171142 A1 | 7/2009 | Chu | |
| 2009/0171143 A1 | 7/2009 | Chu et al. | |
| 2009/0171377 A1 | 7/2009 | Intoccia et al. | |
| 2009/0192346 A1 | 7/2009 | Rosenblatt | |
| 2009/0192347 A1 | 7/2009 | Davila et al. | |
| 2009/0216075 A1 | 8/2009 | Bell et al. | |
| 2009/0222025 A1 | 9/2009 | Catanese, III et al. | |
| 2010/0191045 A1 | 7/2010 | Gobron et al. | |
| 2010/0261955 A1 | 10/2010 | O'Hern et al. | |

OTHER PUBLICATIONS

United States Patent and Trademark Office, Notice of Allowance dated Feb. 12, 2014 in U.S. Appl. No. 12/652,664, 8 pages.
United States Patent and Trademark Office, Office Action dated Jul. 11, 2013 in U.S. Appl. No. 12/652,664, 25 pages.
United States Patent and Trademark Office, Final Office Action dated Jan. 22, 2013 in U.S. Appl. No. 12/652,664, 14 pages.
United States Patent and Trademark Office, Office Action dated Aug. 14, 2012 in U.S. Appl. No. 12/652,664, 14 pages.
WIPO, U.S. International Search Authority, International Search Report dated May 13, 2010 in International Patent Application No. PCT/US2010/020161, 2 pages.
WIPO, U.S. International Search Authority, International Search Report dated May 13, 2010 in International Patent Application No. PCT/US2010/020158, 2 pages.
WIPO, U.S. International Search Authority, International Search Report dated May 13, 2010 in International Patent Application No. PCT/US2010/020151, 2 pages.

* cited by examiner

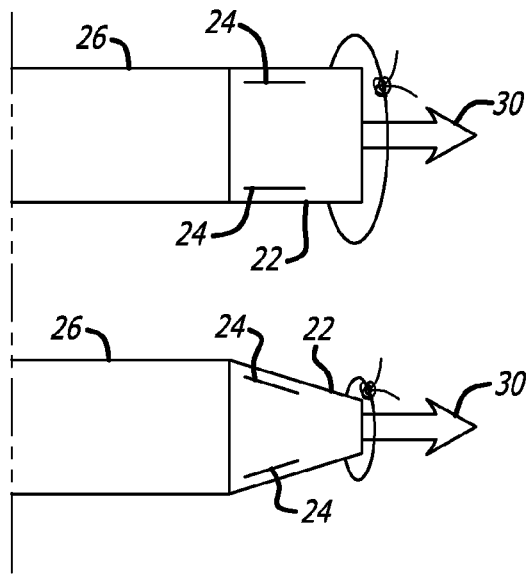
FIG. 11C
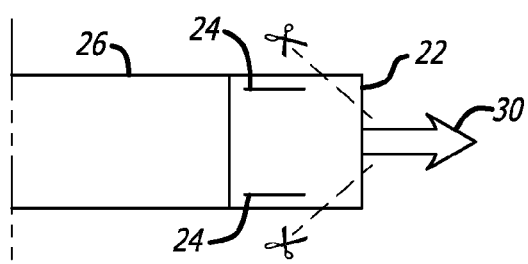
FIG. 11D
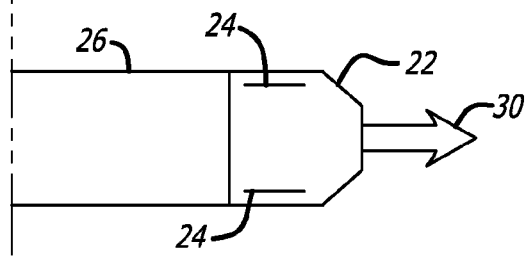

IMPLANTS AND PROCEDURES FOR
SUPPORTING ANATOMICAL STRUCTURES
FOR TREATING CONDITIONS SUCH AS
PELVIC ORGAN PROLAPSE

RELATED APPLICATIONS

This application is a continuation of the U.S. patent application Ser. No. 14/286,953 filed May 23, 2014 entitled Implants And Procedures For Supporting Anatomical Structures For Treating Conditions Such As Pelvic Organ Prolapse, which is a divisional of U.S. patent application Ser. No. 12/652,664 filed Jan. 5, 2010 entitled Implants And Procedures For Supporting Anatomical Structures For Treating Conditions Such As Pelvic Organ Prolapse, which claims priority to U.S. Provisional Application Ser. No. 61/142,604 filed Jan. 5, 2009, entitled Implantable Anchors For Use With Mesh Within The Body, and is related to U.S. application Ser. No. 12/652,640, filed Jan. 5, 2010, entitled Implants And Procedures For Supporting Anatomical Structures For Treating Conditions Such As Incontinence (now abandoned), and U.S. application Ser. No. 12/652,706, filed Jan. 5, 2010, entitled Implants And Procedures For Supporting Anatomical Structures (now abandoned), all of which are hereby incorporated herein by reference in their entireties.

FIELD OF THE INVENTION

The present invention pertains to the field of medical devices for anchoring and supporting anatomical structures and, more particularly, to implantable mesh that are operative to treat pelvic organ prolapse and incontinence.

BACKGROUND OF THE INVENTION

Pelvic floor disorders are a class of abnormalities that affect the pelvic region of millions of men and women. In women, for example, the pelvic region includes various anatomical structures such as the uterus, the rectum, the bladder, and the vagina. These anatomical structures are supported and held in place by a complex collection of tissues, such as muscles and ligaments. When these tissues are damaged, stretched, or otherwise weakened, the anatomical structures of the pelvic region shift and in some cases protrude into other anatomical structures. For example, when the tissues between the bladder and the vagina weaken, the bladder may shift and protrude into the vagina, causing a pelvic floor disorder known as cystocele. Other pelvic floor disorders include vaginal prolapse, vaginal hernia, rectocele, enterocele, uterocele, and/or urethrocele.

Pelvic floor disorders often cause or exacerbate urinary incontinence (UI). One type of UI, called stress urinary incontinence (SUI), effects primarily women and is often caused by two conditions—intrinsic sphincter deficiency (ISD) and hypermobility. These conditions may occur independently or in combination. In ISD, the urinary sphincter valve, located within the urethra, fails to close (or "coapt") properly, causing urine to leak out of the urethra during stressful activity. In hypermobility, the pelvic floor is distended, weakened, or damaged. When the afflicted woman sneezes, coughs, or otherwise strains the pelvic region, the bladderneck and proximal urethra rotate and descend. As a result, the urethra does not close with sufficient response time, and urine leaks through the urethra.

UI and pelvic floor disorders, which are usually accompanied by significant pain and discomfort, are often treated by implanting a supportive sling or mesh in or near the pelvic floor region to support the fallen or shifted anatomical structures or more generally, to strengthen the pelvic region by promoting tissue in-growth. Often, treatments of stress incontinence are made without treating the pelvic floor disorders at all, potentially leading to an early recurrence of the stress incontinence.

Existing systems, methods, and kits for treatment typically employ delivery devices to position a supportive surgical implant into a desired position in the pelvic region. However, some of these systems and methods require a medical operator to create multiple incisions and deliver the implant using complex procedures. Moreover, many existing surgical implants are not suitably sized or shaped to properly fit within a patient and treat pelvic floor disorders. Accordingly, medical operators and patients need improved systems, methods, and surgical kits for the treatment of pelvic floor disorders and/or urinary incontinence.

OBJECTS AND SUMMARY OF THE INVENTION

The present invention provides improved methods and devices for supporting pelvic organs in the treatment of conditions such as incontinence and various pelvic floor disorders including but not limited to cystocele, enterocele and rectocele.

Devices of the present invention include implants having soft, flexible support bodies and anchors that are sturdy and durable.

Other devices of the present invention include introducers that allow an implant to be deeply implanted so as not to cause damage to the pelvic floor and to preserve the natural length of the vagina.

Methods of the present invention include the use of multiple implants for treating multiple disorders, including treating pelvic floor disorders and incontinence.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 11A-11D are plan views of one end of an implant according to certain embodiments of the present invention.

DESCRIPTION OF EMBODIMENTS

Figure 1:
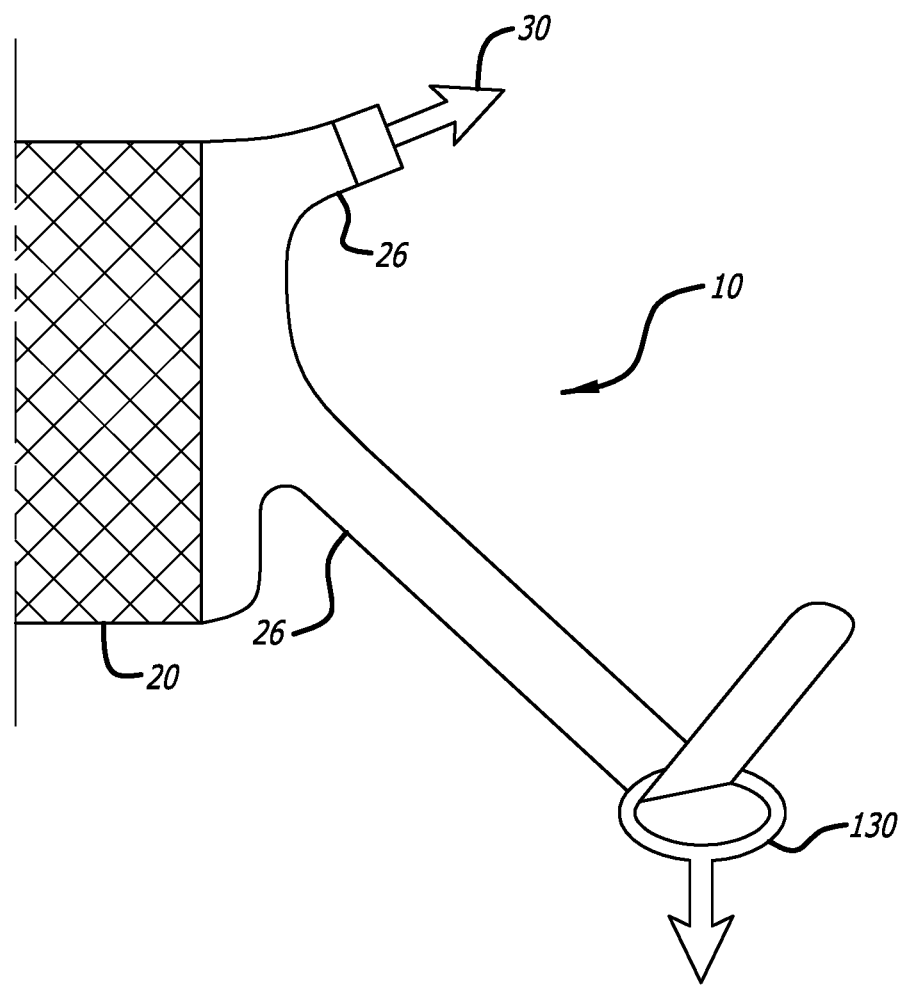
FIG. 1 is a partial plan view of an implant according to an embodiment of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The implant according to the present invention may, for example, be employed to provide support for organs in treatment for conditions such as incontinence and various pelvic floor disorders including but not limited to cystocele, enterocele and recetocel. In this regard, the implant is operative to provide a single-incision solution for implanting a surgical support member within the body specifically for pelvic organ prolapse applications. The implant, the implant delivery system, and the associated methods for implanting the implant provide a strong anchor with a delivery method that is safe, fast, and easy to deploy for surgeons of various experience levels. The present invention allows for easy and controlled deployment of an anchor deep within the body, preferably under palpation control, while providing the ability to easily adjust the mesh tension prior to locking the implant in place.

Figure 2A:
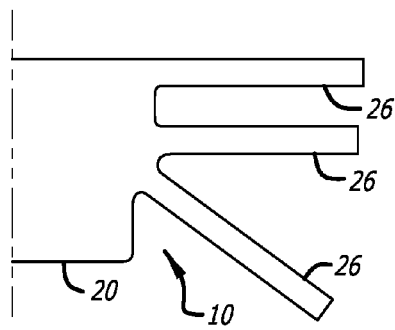
FIG. 2A-2C are partial plan views of an implant according to an embodiment of the present invention.
Figure 2B:
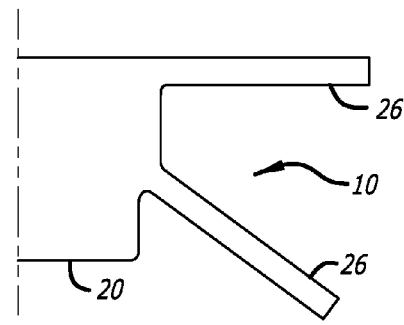
Figure 2C:
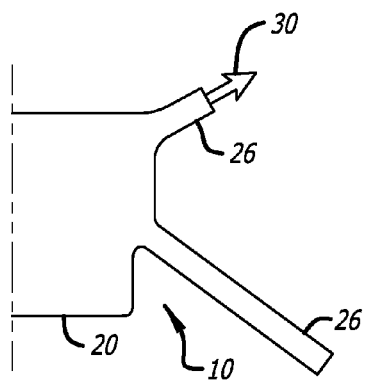
Figure 3:
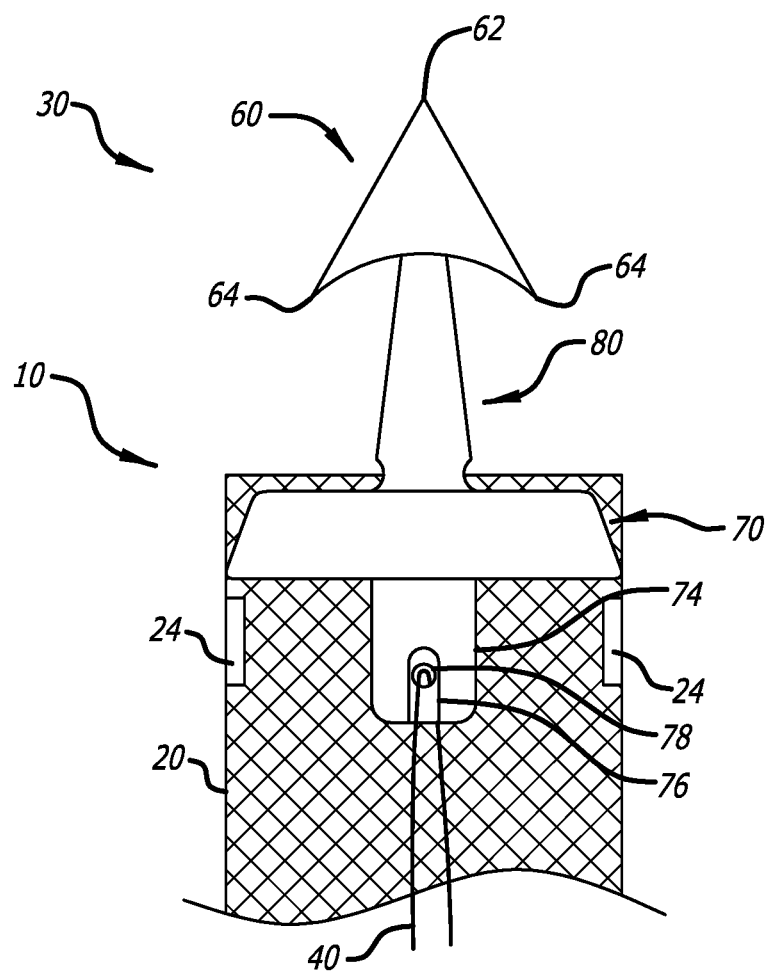
FIG. 3 is a plan view of an implant according to an embodiment of the present invention.
Figure 4:
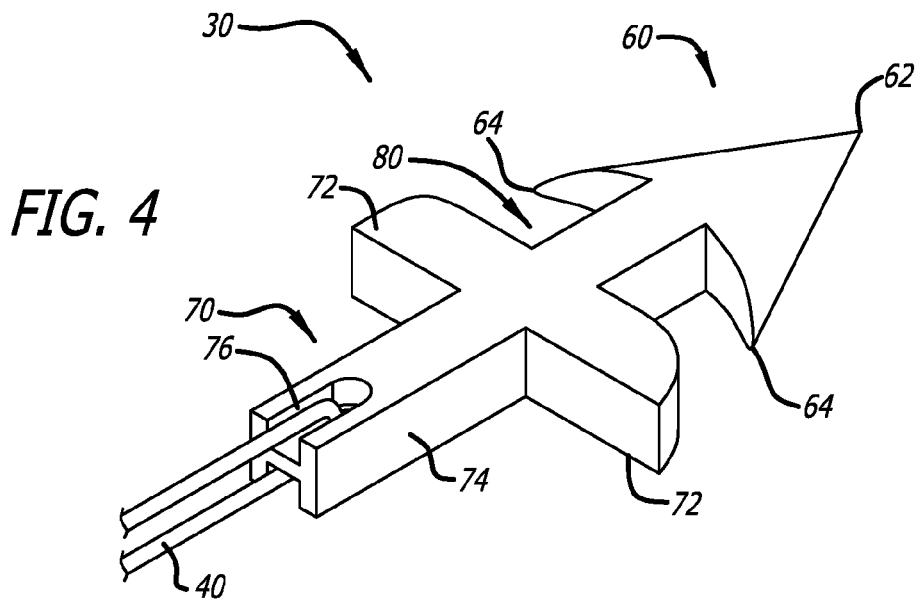
FIG. 4 is a perspective view of an implant according to an embodiment of the present invention.
Figure 5:
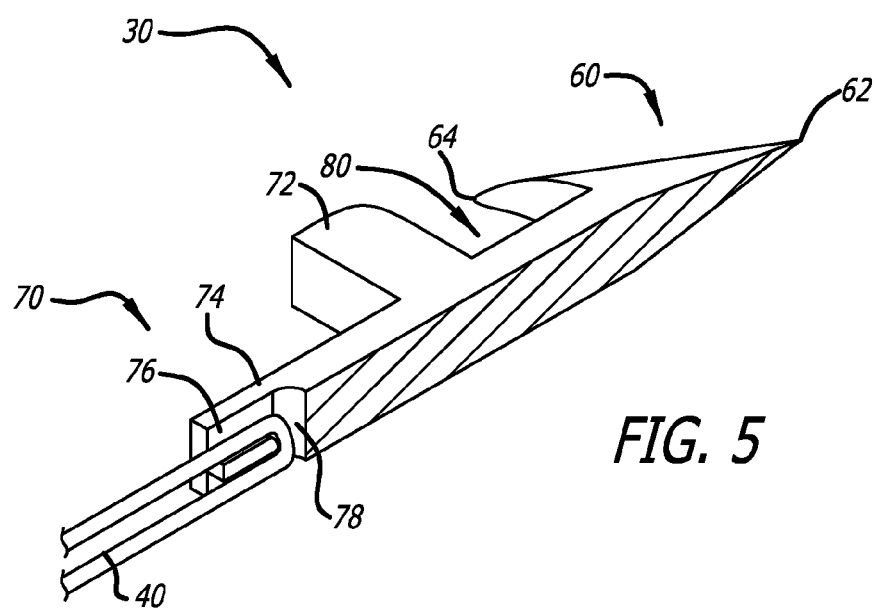
FIG. 5 is a cross-sectional, perspective view of one end of an implant according to an embodiment of the present invention.
Figure 6:
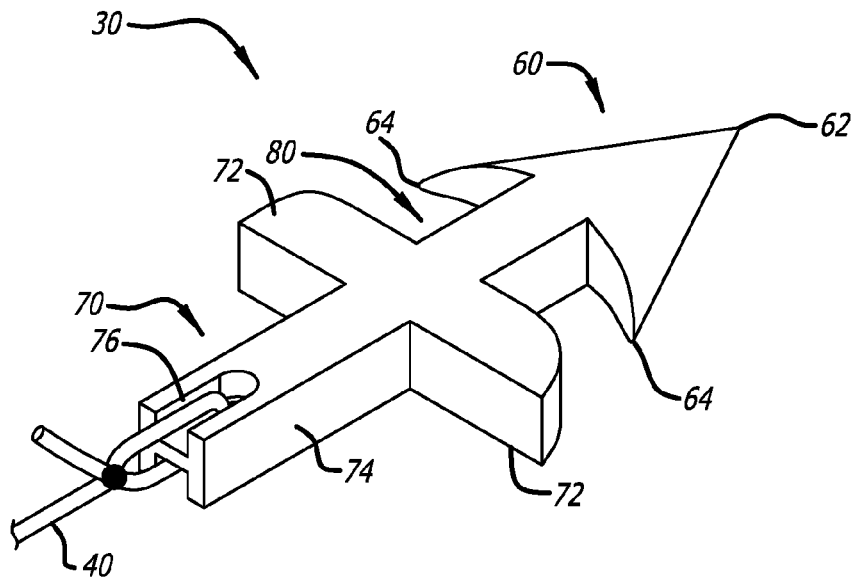
FIG. 6 is a perspective view of an anchor according to an embodiment of the present invention.

Broadly speaking, as shown in FIG. 1, an implant 10 according to certain embodiments of the present invention includes a supporting member 20 having one or more arms 26 associated with an anchor that secures the implant 10 to tissue within the body, e.g. the obturator member (OM), the obturator internus fascia, the obturator internus muscle, the arcus tendineus levator ani, the levator ani muscle, the sacrospinous ligaments (SSL), the illiococcygeus muscle, or the arcus tendineus facia pelvis (white line). For the sake of clarity, FIGS. 1-2 show only one side of the implant 10. It is understood that the side not shown is a mirror image of the side shown. FIGS. 2A-2C show alternative configurations of the supporting member 20 and the arms 26. Suitable supporting members 20 are further described in the Assignee's U.S. patent application Ser. No. 11/936,063, the contents of which are herein incorporated by reference. In certain embodiments of the present application, the supporting member 20 has a simpler shape that is approximately rectangular, oval, or circular and in which the arms 26 are less pronounced or even absent.

The support member 20 may be fabricated of a synthetic material, such as surgical mesh and the like, natural tissues, such as tissues harvested from either an animal, cadaverous source or the patient himself, and/or combinations of synthetic and natural materials. In a preferred embodiment, the support member 20 is fabricated of a mesh or weave.

Figure 16:
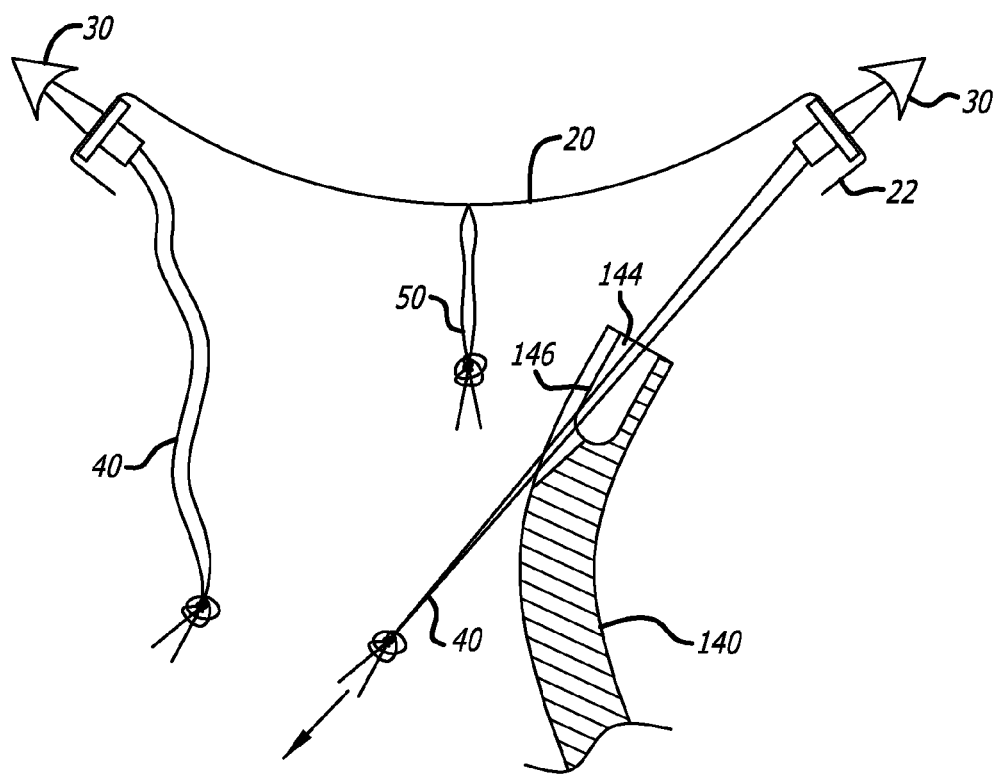
FIG. 16 is a perspective view of and implant and a delivery system according to an embodiment of the present invention.

In certain embodiments, a support member suture 50, shown in FIG. 16, is advantageously attached to the support member 20. The support member suture 50 is looped through, tied to, or otherwise associated with the support member 20. Preferably, the support member suture 50 is affixed to the support member 20 at a proximate mid-point of the support member 20. As would be understood by one of ordinary skill in the art, it may also be advantageous to employ a plurality of the support member sutures 50 at predetermined positions on or within the support member 20 in order to provide a plurality of markers along a dimension of the support member 20. In order to distinguish the various individual sutures, the sutures may be provided in different colors, lengths, or other indicating means that would allow a user to distinguish one suture from another. Indicating marks may also be provided along a length of the suture that can be employed to determine a depth of the suture within the body.

Turning next to the tissue anchoring element of the implant 10 of the present invention. Each of the below disclosed anchors includes a tissue piercing portion and a proximal portion having an element for associating the anchor with the support member 20.

FIGS. 3-7 show an anchor 30 according to one embodiment of the present invention. The anchor 30 has a distal portion 60 and a proximal portion 70 associated with one another by mid-portion 80. A proximal end of the distal portion 60 of the anchor 30 is associated with or attached to a distal end of the mid-portion 80. Conversely, a distal end of the proximal portion 70 is associated with or attached to a proximal end of the mid-portion 80 of the anchor 30. The mid-portion 80 of anchor 30 is formed as a shaft or spacer that serves to provide space between the distal portion 60 and the proximal portion 70 to, for example, accommodate a depth of tissue through which the distal portion 60 has penetrated.

Figure 7:
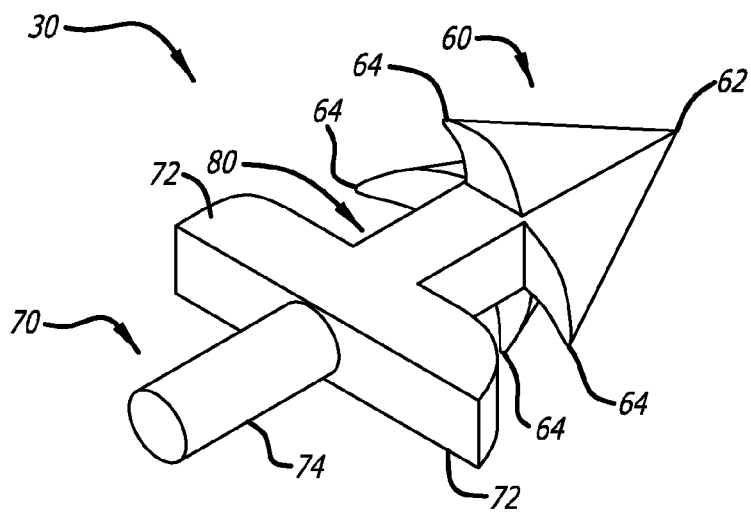
FIG. 7 is a perspective view of an anchor according to an embodiment of the present invention.

The distal portion 60 of the anchor 30 employs a piercing tip 62 for penetrating tissue and a tissue-retention protrusion 64 proximal of the piercing tip 60 that anchors or secures the distal portion 30 within tissue. The distal portion 60 may have, for example, an arrowhead-like shape as shown in FIGS. 3-6. Alternatively, distal portion 60 may have a more complex shape configured to employ more than two, for example as shown in FIG. 7, four tissue-retention protrusions 64. The distal portion 60 may further employ a conical or cone-like shape having a circular tissue-retention protrusion 64. One of ordinary skill in the art would recognize that alternative shapes and configurations of the distal portion 60 are possible while still achieving the desired objective. For example, distal portion 60 may employ resilient, spring loaded and/or self-tensioning tissue-retention protrusions 64.

The proximal portion 70 of anchor 30 comprises a shoulder 72 for providing a back-stop for the support member 20 and a guide member 74 for engagement with a delivery system, as discussed in greater detail below. The proximal portion 70 may further employ recesses 76 and eyelet 78. The anchor suture 40 passes through the eyelet 78 and is, for example, secured back to itself to form a loop. The recesses 76 may be positioned on one or both side of the eyelet 78 and configured so as to accept the anchor suture 40 such that the presence of the anchor suture 40 does not add to or change an outer dimension of the guide member 74.

Figure 8A:
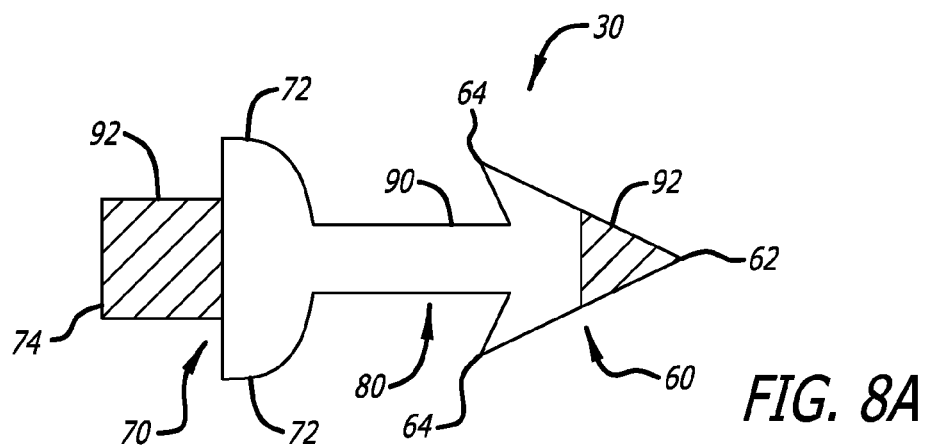
FIGS. 8A and 8B are cross-sectional views of an anchor according to an embodiment of the present invention.
Figure 8B:
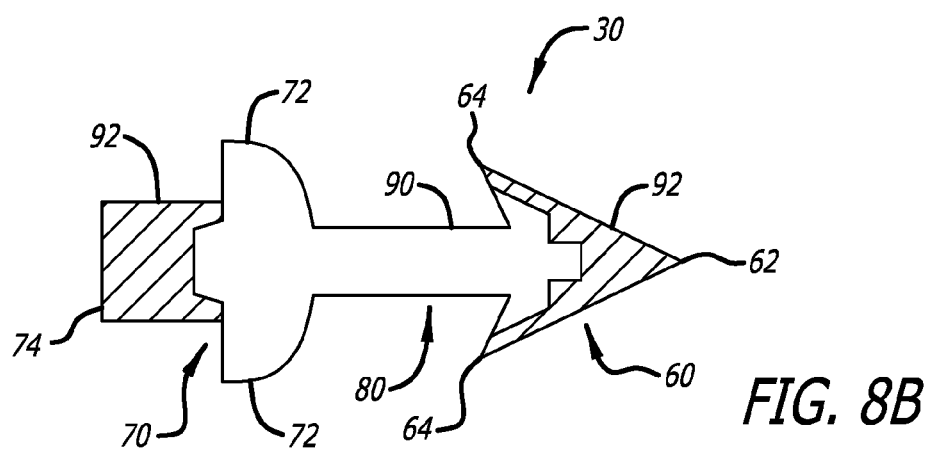
Figure 9A:
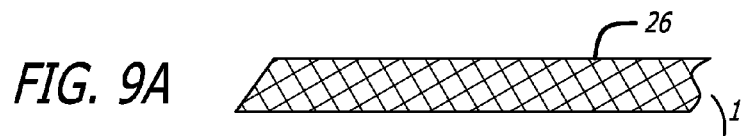
FIGS. 9A-9F is a series of drawings showing a process of assembling an implant according to an embodiment of the present invention.
Figure 9B:
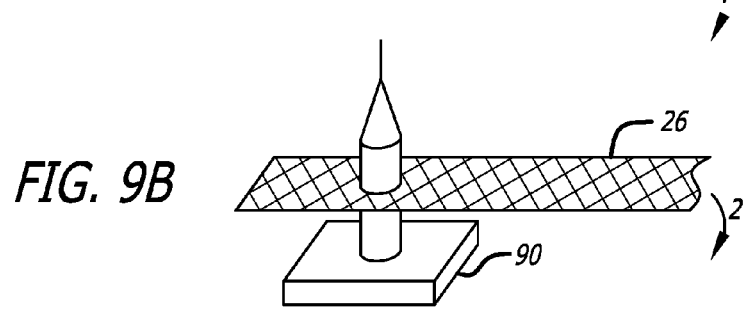
Figure 9C:
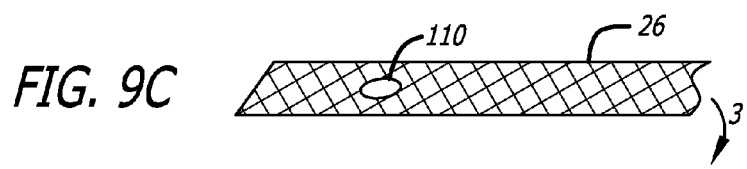
Figure 9D:
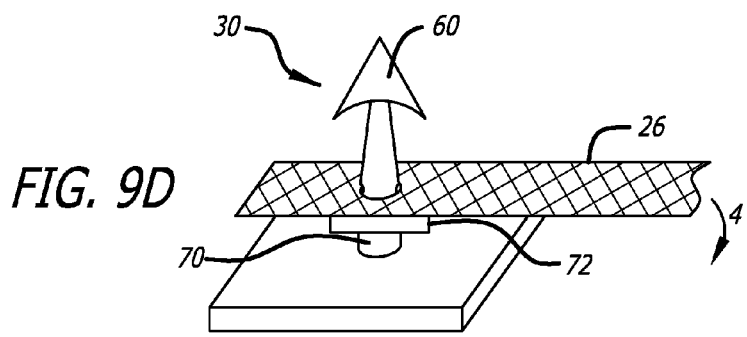
Figure 9E:
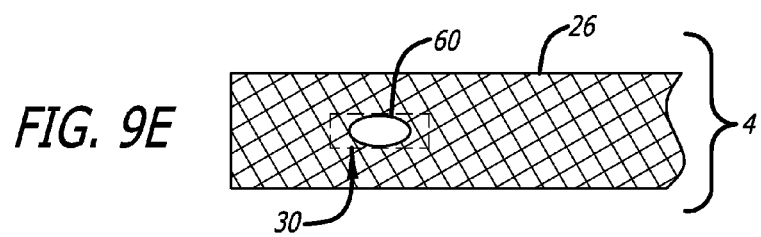
Figure 9F:
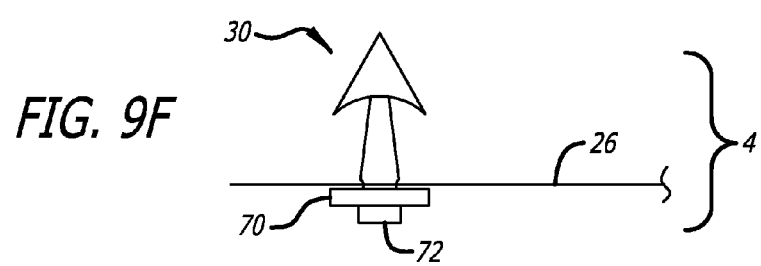
Figure 10A:
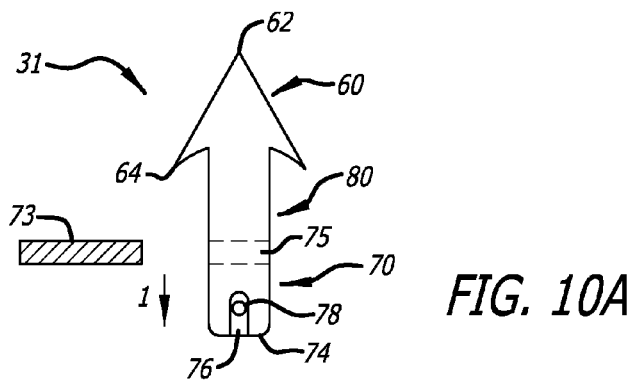
FIG. 10A is a plan view of an anchor according to an embodiment of the present invention.
Figure 10B:
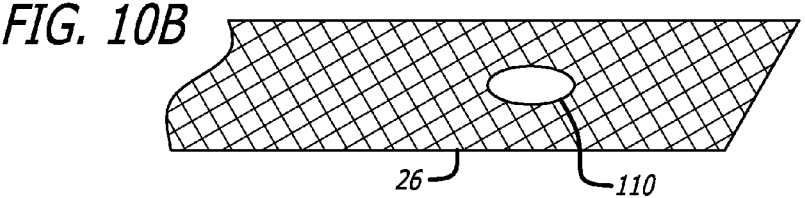
FIGS. 10B-10D is a series of drawings showing a process of assembling an implant according to an embodiment of the present invention.
Figure 10C:
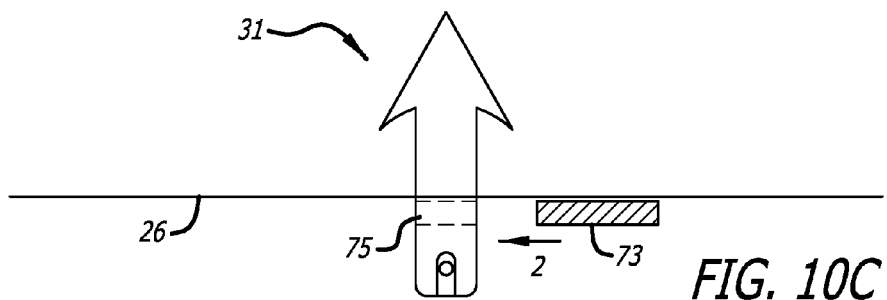
Figure 10D:
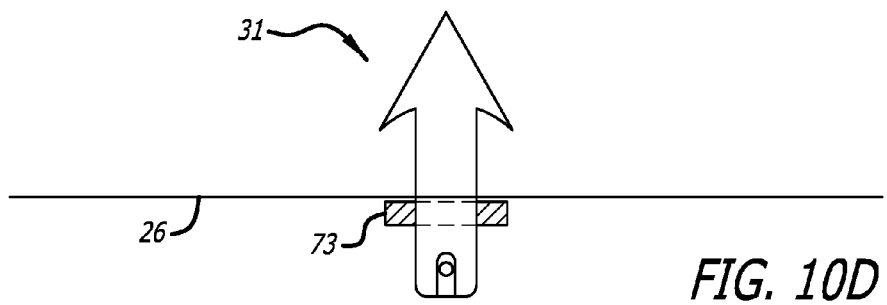

The anchor 30 may be formed from a variety of materials, including but not limited to metal alloys, such as titanium, stainless steel, or cobalt-chome alloys, polymeric materials, such as polyethylene (PE), polypropylene (PP), polysulfone, polyether ether ketone (PEEK), polyether imide (PEI), and biodegradable materials, such as polylactic acid (PLA) and polyglycolic acid (PGA) based materials. The anchor 30 may be formed of a single material or a combination thereof. For example, as illustrated in FIGS. 8A and 8B, the anchor 30 may be formed of a combination of primary material 90, such as titanium, and a biodegradable material 92, shown in as hashed, assembled or molded over the primary material 90.

Turning next to FIGS. 9A-9F, FIGS. 9A-9F show the steps of assembling the implant 10 according to various embodiments of the present invention. For the sake of clarity, FIGS. 9A-9F show only the assembly of one arm 26 of the implant 10. First, a tool 90 is used to form an opening 110 through the arm 26 proximate an end of the arm 26 by penetrating, stretching, or spreading the mesh or knitted material of the arm 26 of the support member 20. The tool 90 has a tapered or pointed end and a cross-section shape in the form of a circle, rectangle, oval or most any other shape. The distal portions 60 of the anchors 30 are then inserted through the openings 110 in the arm 26 until the arm 26 rests against the shoulders 72 of the proximal portions 72 of the anchors 30. In a preferred embodiment, the openings 110 are formed interior of the outer perimeter of the arm 26 such that there is sufficient material of arm 26 so that the openings 110 do not substantially expand or rip though the outer perimeter of the support member 20.

In an alternative embodiment of the present invention, as shown in FIG. 10A-10D, the shoulder of the anchor 31 is formed of a plastic or metal pin 73 that is inserted through a receiving hole 75 formed through the proximal portion of the anchor 31. During assembly of the implant 10, once the openings 110 are formed through the arm 26, the guide 74 and/or proximal portion 70 of anchor 31 is placed through the opening 110 and the pin 73 is inserted through the receiving hole 75 to form an element functionally similar to the shoulder 72 previously described. As one of ordinary skill in the art would recognize, this embodiment provides the advantage that a smaller opening 110 may be formed when assembling the implant 10. The smaller opening 110, in turn, provides the advantage of the arm 26 having a greater resistance to tearing and deformation.

Figure 11A:
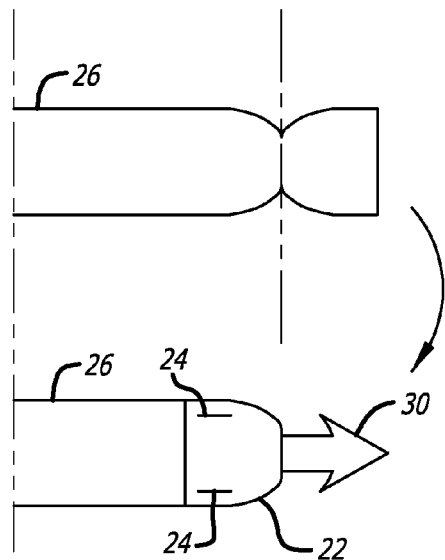
Figure 11B:
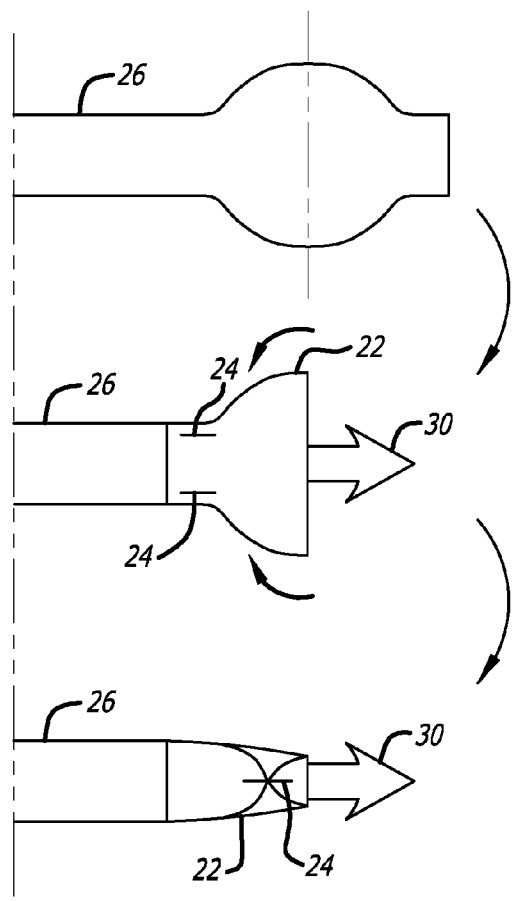

In certain other embodiments of the present invention, the assembled implant 10 as described above may be subjected to additional fabrication steps. For instance, as shown in FIGS. 11 and 12, after insertion of the anchor 30 through the opening 110 of arm 26, a portion of the arm 26 between the opening 10 and the outer perimeter of the arm 26 is folded over the shoulder of the anchor 30 back on to itself to form a folded portion 22. The folded portion 22 may then be bonded, sutured, welded, or tacked to it self to form bond 24 to better maintain the fold. Formation of the folded portion 22 serves, in part, to decrease resistance to penetration of the anchor 30 into tissue. The fold 22 may additionally help insure that the anchor 30 remains inserted through the arm 26 during handling and implantation of the implant 10, as well as provide a more visually appealing appearance to the implant 10. As shown in FIGS. 11 and 12, the shape of the portion of the arm 26 that forms the fold 22 may be manipulated so as to, for example, result in the arm 26 having a tapered end. A tapered end may be formed by forming a portion of the arm 26 so as to have a width that narrows at a fold line 26, as shown in FIG. 11A. A tapered end may also be formed through a secondary folding of the extremities or corners of the fold 22 towards one another, as shown in FIG. 11B. Alternatively, as shown in FIG. 11C, once the folded portion 22 is formed a suture may be threaded through the fold 22 and cinched and bound to itself so as to form a tapered end of the anchor 30. A tapered end may also be formed in the implant 10 by cutting or trimming the corners of the fold 22 after the fold 22 has been formed, as shown in FIG. 11D.

Figure 12A:
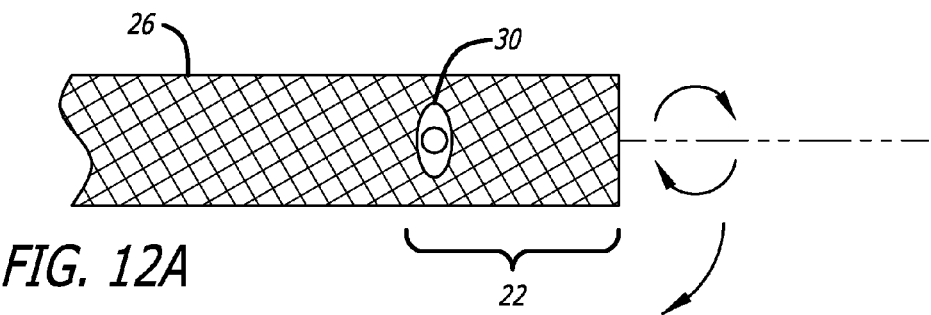
FIGS. 12A-12C is a series of drawings showing a process of assembling an implant according to one embodiment of the present invention.
Figure 12B:
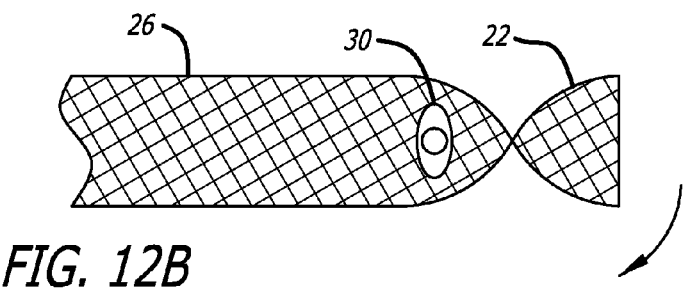
Figure 12C:
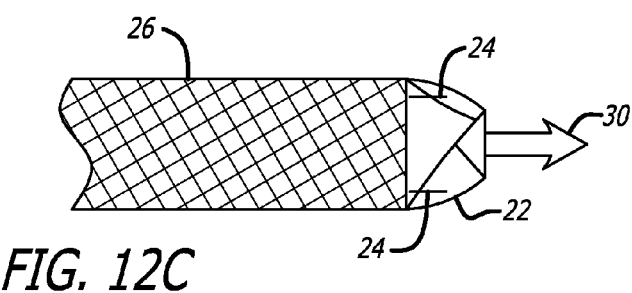

FIGS. 12A-12C show yet another embodiment of the implant 10 in which, prior to formation of the fold 22, the arm 26 is twisted 180 degrees or more. Again, this method of assembly decreases resistance to penetration of the anchor and helps ensure that the anchor 30 remains inserted through the arm 26 during handling and implantation. One of ordinary skill in the art will, however, recognize that other methods of assembling the support member 20 and the anchor 30 to achieve the desired characteristics of the implant 10 are known in the art.

Figure 13A:
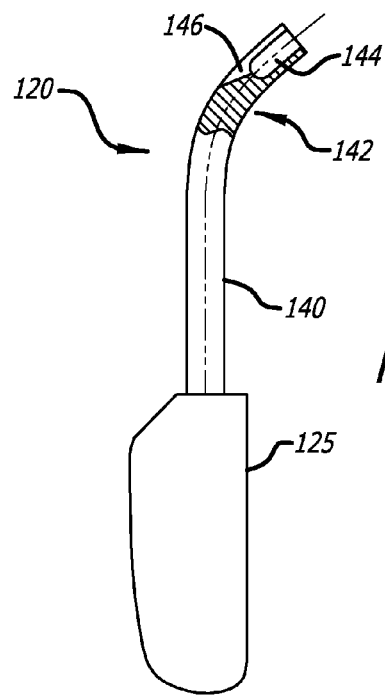
FIG. 13A is a side elevation view and a cut-away view of a delivery system according to an embodiment of the present invention.

Turning now to the delivery system of the present invention. Broadly speaking, the delivery system is configured to receive a portion of the anchor 30 of the assembled implant 10. FIG. 13A shows a delivery system 120 having a handle 125 and a shaft 140. The handle 125 is preferably ergonomically shaped to facilitate grasping and manipulating. The handle 125 is preferably marked, colored, textured or otherwise configured so as to indicate to a user the orientation of the delivery system 120. The shaft 140 protrudes from or is an extension of the handle 125. The shaft 125 is, for example, formed of stainless steel or other metal in the general shape of a needle. A curved distal portion 142 of the shaft 140 includes a cavity 144 and a slot 146.

Figure 13B:
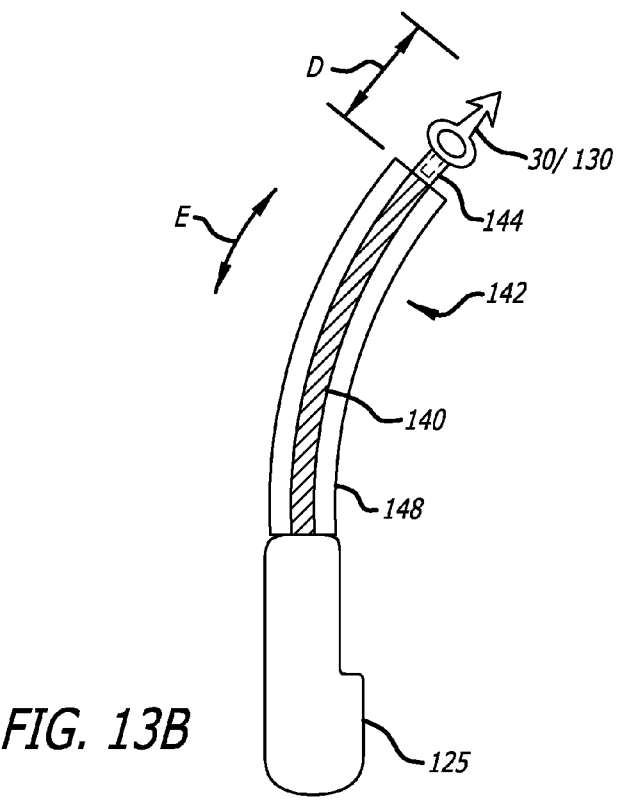
FIG. 13B is a cross-sectional view of a delivery system according to an embodiment of the present invention.

Optionally, as shown in FIG. 13B, the delivery system 120 may further employ a sheath 148. The sheath 148 is a slit tube or u-shaped channel that functions, in part, to protect the support member 20 and various associated sutures from exposure to tissue during implantation. The sheath 148 also functions to limit the depth of penetration of the anchor 30 in to the target tissue. This function is achieved by configuring the sheath 148 to be a distance D shorter than a length of the implant 10 and shaft 140 when assembled and have an outer diameter greater than that of the shaft 140 and the anchor. Because the sheath 148 is displaceable along the axis of the shaft 140, arrow E of FIG. 13B, the user, after first piercing the target tissue with the distal portion 60 of the anchor 30, may move the sheath to determine or measure the approximate depth of that the anchor 30 within the target tissue.

Figure 14:
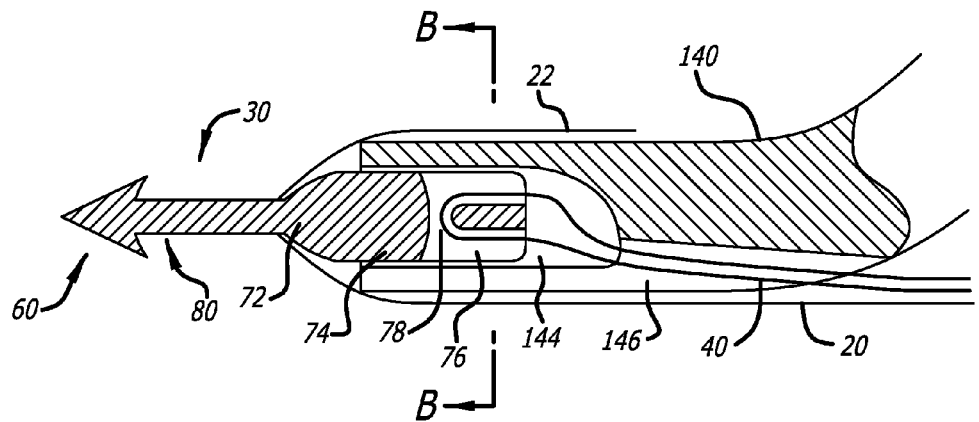
FIG. 14 is a cross-sectional view of a delivery system according to an embodiment of the present invention.
Figure 15:
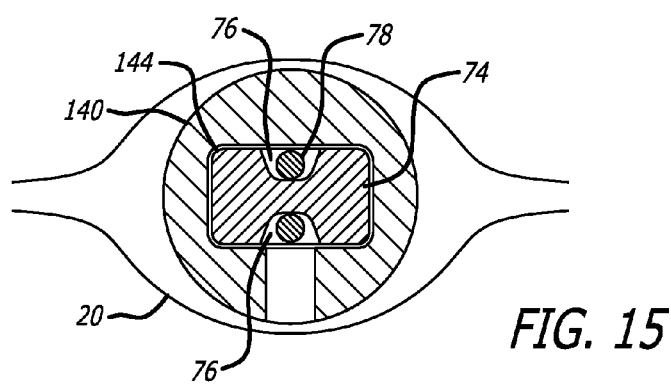
FIG. 15 is a cross-sectional view of a delivery system taken along section line B-B of FIG. 14.

Referring now to FIGS. 14 and 15, FIG. 14 shows the implant 10 and delivery system 120 assembled ready for implantation of the implant 10. FIG. 15 shows a cross-sectional view of the assembled implant 10 and delivery system 120 viewed along section line B-B of FIG. 14. As will be noted, the shape of the cavity 144 corresponds to the shape of the guide 74 of the anchor 30. That is to say that the guide 74 of the anchor 30 of the implant 10 and the cavity 144 of the shaft 140 of the delivery system 120 are complementary elements, the cavity 144 forming a female receiving element for the male guide 74. Preferably, the cavity 144 and the guide 74 are formed in the shape of a square, rectangle, oval, triangle, star, or other shape that resists the guide 74 rotating within the cavity 144. In certain embodiments of the present invention, the cavity 144 and the guide 74 form a friction fit such that the guide 74 is maintained within the cavity 144 during handling and deployment of the implant 10 but is readily released from the cavity 144 upon engagement of the distal portion 60 of the anchor 30 with tissue. A portion of the slot 146 penetrates radially through the shaft 140 into the cavity 174 and extends axially along a length of the distal portion 142 of the shaft 140. Preferably, the slot 146 extends axially along the shaft 140 to a greater extent than the cavity 174. The slot 146 thereby receives and forms a channel through which the anchor suture 40 of anchor 30 is positioned along an axis of the shaft 140.

A method for deploying or implanting the implant 10 incorporating the anchors 30 will now be described. First, a single incision or entry point is made in the patient followed by blunt dissection as necessary or desired. One side of the implant 10 incorporating the anchor 30 that is engaged with the delivery system 120 is then inserted through the entry point and the anchor 30 that is engaged with the delivery system 120 is forced into or through a portion of the target tissue, e.g. the transobturator, the obturator internus fascia, the obturator internus muscle, the obturator member (OM), the arcus tendineus levator ani, or levator ani muscle. The delivery system 120 is retracted away from the anchor 30 that has penetrated the target tissue thereby breaking the engagement between the delivery system 120 and the anchor 30. During this process and particularly while the delivery system 120 is being retracted, the user secures the corresponding anchor suture 40 such that the delivery system 120 is retracted while an end of the anchor suture 40 is maintained extending out from the entry point. The arm 26 of a second, opposite side of the implant 10 that is engaged with the delivery system 120 is then implanted as described with regard to the first side.

Substantially concurrent with the implantation of the second side of the implant 10, the support member 20 of the implant 10 is positioned so as to support at least a portion of the desired organ. The support member suture 50, shown in FIG. 16, may be used to determine the position and/or tension of the implanted support member 20. The tension of the support member 20 spanning between the two sides of the implant 10 incorporating the anchors 30 is initially adjusted by pushing the delivery system 20 engaged with the anchor 30 of the second arms 26 of the implant 10 further into the target tissue. The delivery system 120 is then retracted from the second arm 26 of the implant 10. An end of the second anchor suture 30 is also maintained such that it extends out from the entry point.

Should it be determined that greater tension is desired or if it is otherwise desirable to reengage of the delivery system 120 with one of the anchors 30, the present invention provides a particularly advantageous means for achieving such. As shown in FIG. 16, the end of the anchor suture 40 of the relevant anchor 30 that extends from the entry point is tensioned and secured. The slot 146 of the delivery system 120 is then positioned such that the anchor suture 40 passes through the slot 146, and serves as a guide for the delivery system 120 to the relevant anchor 30. The delivery system 120 is advanced towards the relevant anchor 30 along the anchor suture 40. The guide 74 of the anchor 30 is thereby received by the cavity 144 of the delivery system 120 and, if desired, the friction fit between the anchor 30 and the delivery system 120 is reestablished. It is then possible to adjust the tension of the support member 20 of the implant 10 by pushing the delivery system 120 so as to drive the anchor further into the target tissue. The implant can be retracted by pulling upon the suture thereby releasing all or a portion of the tension present in the implant 10.

Upon completion of the implantation of the implant 10, the anchor sutures 40 and support member sutures 50 can be left in place for possible use in a follow-up procedure or may be removed from the patient.

FIGS. 17-24 show an anchor 130 according to another embodiment of the present invention. The anchor 130 has a distal portion 60 and a proximal portion 70 associated with one another by mid-portion 80. A proximal end of the distal portion 60 of the anchor 130 is associated with or attached to a distal end of the mid-portion 80. Conversely, a distal end of the proximal portion 70 is associated with or attached to a proximal end of the mid-portion 80 of the anchor 130. The mid-portion 80 of anchor 130 is formed as a shaft or spacer that serves to provide space between the distal portion 60 and the proximal portion 70 to, for example, accommodate a depth of tissue through which the distal portion 60 has penetrated.

The distal portion 60 of the anchor 130 employs a piercing tip 62 for penetrating tissue and one or more tissue-retention protrusions 64 proximal of the piercing tip 60 that anchor or secures the distal portion 130 within tissue. The distal portion 60 may have, for example, an arrowhead-like shape as shown in FIGS. 17-24. Alternatively, the distal portion 60 may have a more complex shape and configuration as described above, and shown in FIG. 7, regarding the anchor 30 disclosed above.

Figure 17:
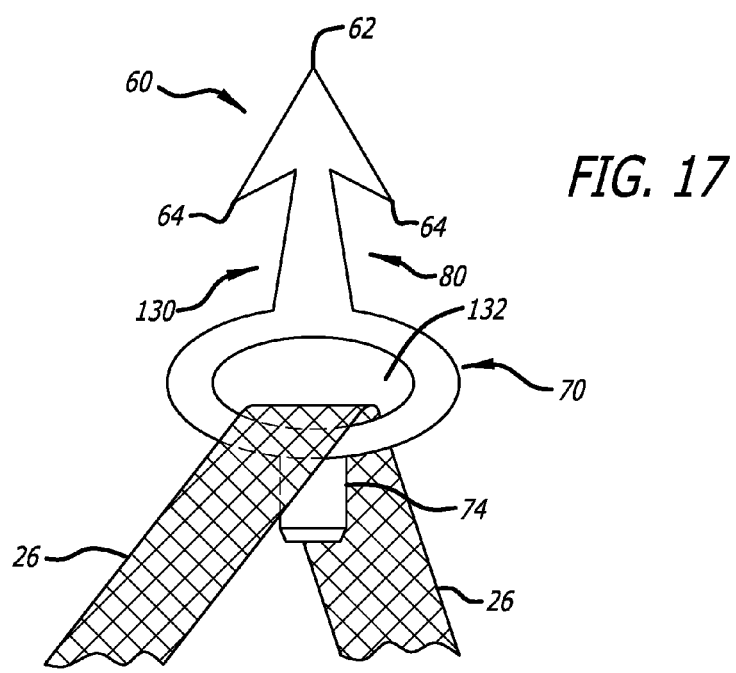
FIG. 17 is a plan view of an anchor according to an embodiment of the present invention.
Figures 18A, 18B:
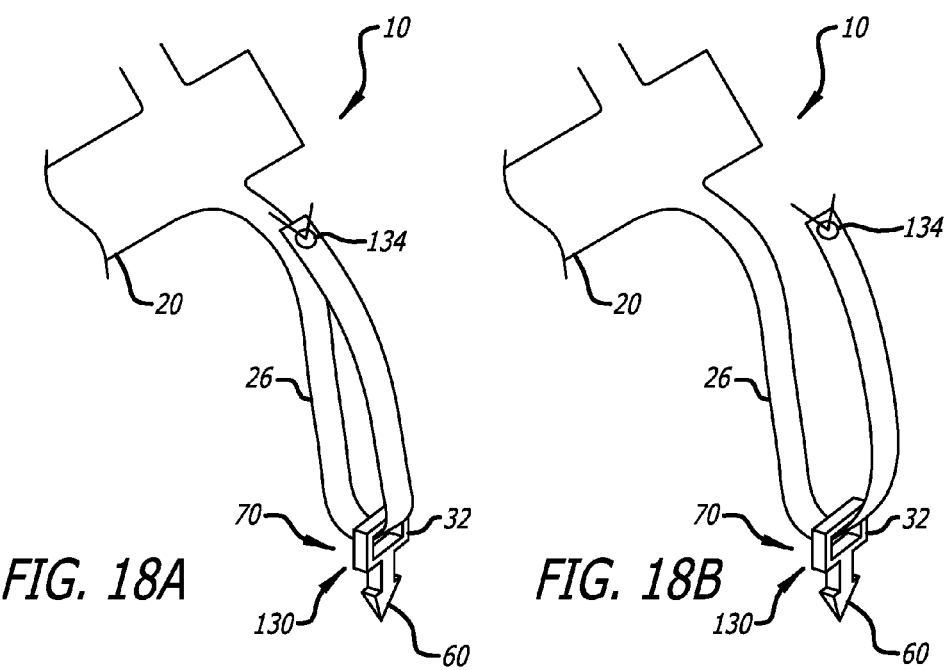
FIGS. 18A and 18B are partial perspective views of an implant according to an embodiment of the present invention.

As shown in FIG. 17, the proximal portion 70 of anchor 130 comprises an aperture 132 for receiving a portion of the support member 20, the arm 26 of the support member 20, or a suture and may optionally comprise a guide member 74 for engagement with a delivery system. The guide member 74 of the anchor 130 may function and be configured as described above regarding the anchor 30 disclosed above. Accordingly, implantation of the implant 10 incorporating the anchor 130 may be achieved substantially as described above regarding implantation of the implant 10 incorporating the anchor 30. However, as will become apparent from the following description, the implant 10 incorporating the anchor 130, provides certain alternative methods and systems for adjusting the tension of the support member 20 spanning between two anchors 130.

The anchor 130 may be formed from a variety of materials, including but not limited to, titanium, metal alloys, polyethylene (PE), polypropylene (PP), polysulfone, polyether ether ketone (PEEK), polyether Imide (PEI) or other suitable plastic, polymer, and biodegradable materials. As described above with respect to the anchor 30 shown in FIGS. 8A and 8B, the anchor 130 may also be formed of a single material or a combination thereof. The overall size of the anchor 130 is approximately 1-30 mm long and 1-25 mm wide, and preferably 5-15 mm long and 5-15 mm wide.

As shown in FIGS. 17-25, the aperture 132 of the anchor 130 may, for example, be circular, rectangular, or ellipsoidal in shape. In certain embodiments, as shown in FIGS. 17, 18A and 18B, 22A and B, and 23, an interior surface of the aperture 132 is substantially smooth thereby allowing the support member 20 or arm 26 to pass freely through the aperture in either direction. In such embodiments, as shown in FIGS. 18A and 18B, the end of the support member 20 or arm 26 that passes through the aperture 132 is secured back to itself, to another anatomical structure, or a combination thereof in order to tension the implant 10.

Figure 19:
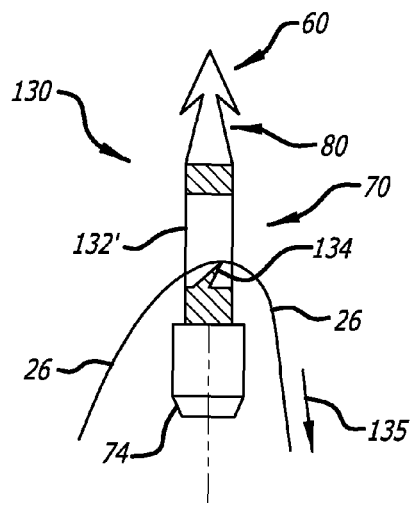
FIG. 19 is a cross-sectional view of an anchor according to an embodiment of the present invention.
Figure 20:
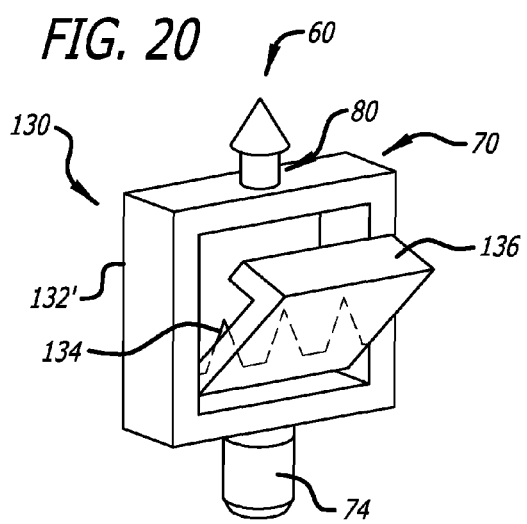
FIG. 20 is a perspective view of an anchor according to an embodiment of the present invention.

Alternatively, as shown in FIGS. 19-21 and 24, the anchor 130 may employ an aperture 132' having teeth or other surfaces that form an engagement member 134 that projects substantially towards an interior of the aperture 132'. As shown in FIG. 19, the engagement member 134 may be angled to one side such that the support member 20 or the arm 26 slides freely in the direction of the arrow 135 through the aperture 132' but is prevented from sliding in the opposite direction due to engagement with the angled engagement members 134. FIG. 20 shows another embodiment of the anchor 130 incorporating the engagement members 134 in which a cover 136 is employed. The cover 136 is incorporated into the proximal portion 70 of the anchor 130 but attachment using a hinge or similar element allowing the cover 136 to be opened and closed. The cover 136 functions to lock the support member 20 or arm 26 into place through the aperture 132', as well as to protect the engagement members 134 such that the engagement members do not become entangled with other structures within the body or tools used during the implantation procedure.

Figure 21:
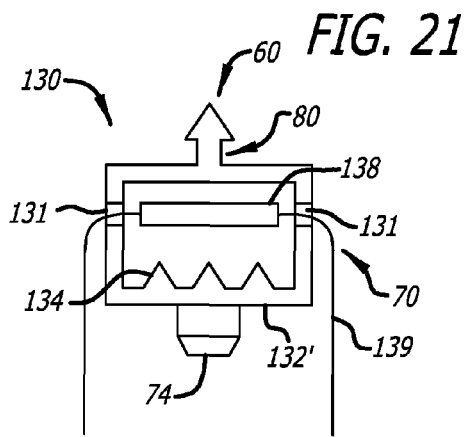
FIG. 21 is a plan view of an implant according to an embodiment of the present invention.

FIG. 21 shows an alternative embodiment of the present invention in which a tube 138 and suture 139 are employed so as to further facilitate engagement and disengagement of the support member 20 or arm 26 and the engagement members 134. The suture 139 enters the aperture 132' through a first hole 131 in the structure forming the aperture 132' above the engagement members 134. The suture 139 then passes through the tube 138 that is sized to move freely within the aperture 132', exits the tube 138, and exits the aperture 132' through a second hole 131 in an opposite side of the structure forming the aperture 132'. The suture 139 is fixed to itself so as to form a loop. An end of the suture 139 is left to extend from the entry point.

In operation, the suture 139 is maintained without tension and the support member 20 or the arm 26 is passed through the aperture 132' and tensioned such that the support member 20 or the arm 26 engages the engagement members 134 and thereby becomes locked in place. Since the suture 139 is not tensioned, tube 138 is free to move and is pulled by the support member 20 or the arm 26 toward and beyond the engagement members 134 as the support member 20 or the arm 26 engages the engagement members 134. Should it be determined that the tension of the support member 20 or the arm 26 needs to be adjusted the support member 20 or the arm 26 are disengaged from the engagement members 134 by tensioning the suture 139 thereby lifting the support member 20 or the arm 26 off of the engagement members 134. The tension of the support member 20 or the arm 26 is adjusted while maintaining tension upon the suture 139. Following adjustment of the tension of the support member 20 or the arm 26, the tension on the suture 139 is released thereby reengaging the support member 20 or the arm 26 with the engagement members 134.

Figure 22A:
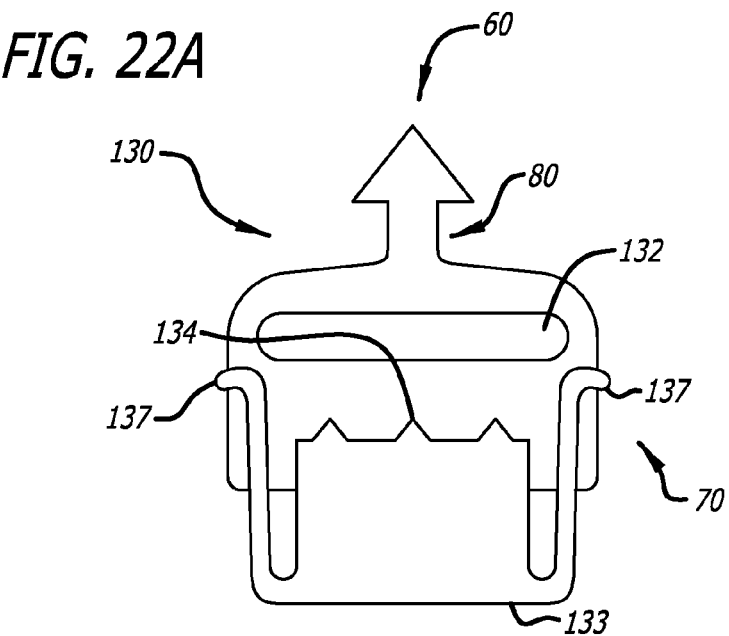
FIGS. 22A and 22B are plan views of an anchor according to an embodiment of the present invention.
Figure 22B:
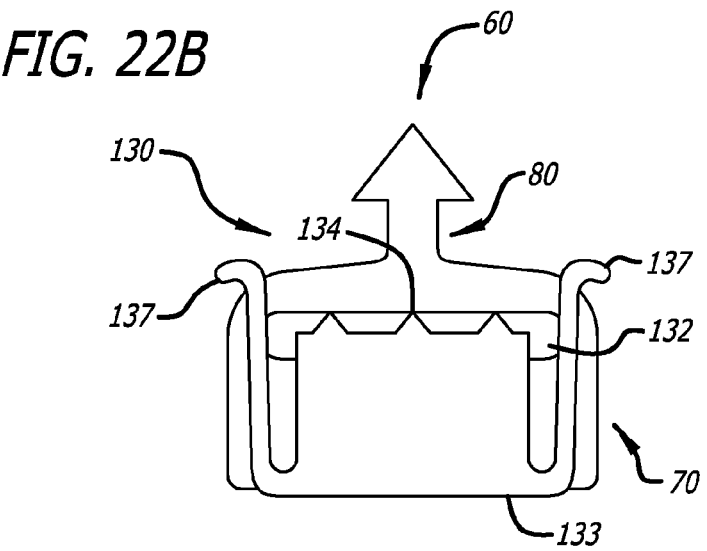

FIGS. 22A and 22B show yet another embodiment of the anchor 130 of the present invention in which the anchor 130 incorporates a slide lock 133 having engagement members 134. The slide lock 133 is incorporated into and integral with the anchor 130 such that the slide lock 133 slides laterally away from and towards the aperture 132. In the open or unlocked state, shown in FIG. 22A, the slide lock 133 is withdrawn or cleared from the aperture 132 and the support member 20 or the arm 26 is passed through the aperture 132 freely. In the locked or closed state, shown in FIG. 22B, the slide lock has been displaced so as to extend into and/or across the aperture and thereby engage the support member 20 or the arm 26 with the engagement members 134 of the slide lock 133. In order to maintain the slide lock in the closed state, the slide lock may incorporate resilient portions 137 that slide into receiving elements or other structural features that prevents the slide lock from further movement absent disengagement of the resilient portions 137 from the receiving elements. One of ordinary skill in the art will recognize that there are various known structures and configurations possible for achieving the above described embodiment, for example, the slide lock may slide within a channel formed in proximal portion 70 of anchor 130 and the resilient portions 137 may engage openings or recesses formed within the channel so as to lock the slide lock into a fixed position.

Figure 23:
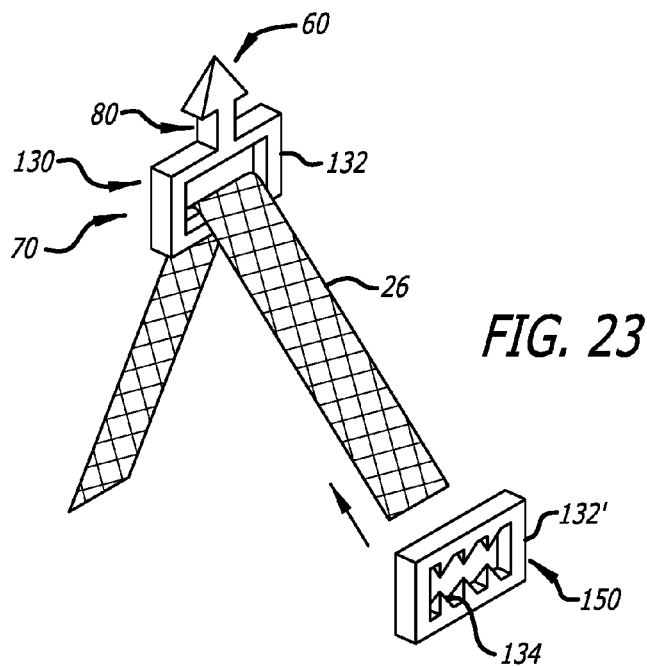
FIG. 23 is a perspective view of an anchor according to an embodiment of the present invention.
Figure 24:
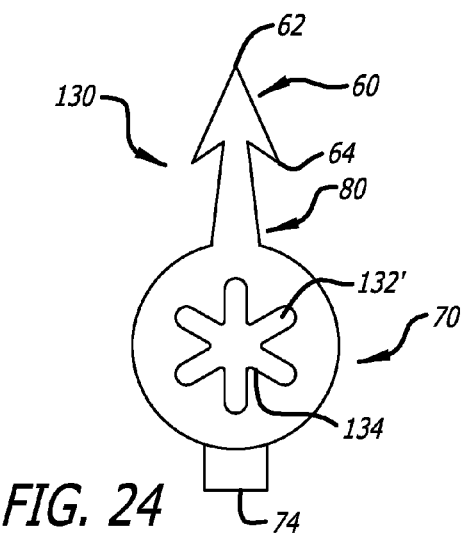
FIG. 24 is a plan view of an anchor according to an embodiment of the present invention.
Figure 25:
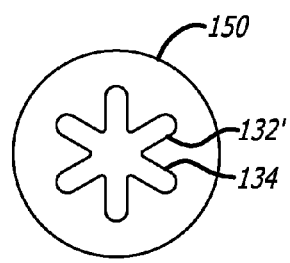
FIG. 25 is a plan view of a locking member according to an embodiment of the present invention.
Figure 26A:
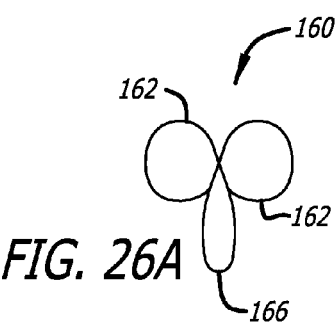
FIG. 26A-26D are plan views of an anchor according to an embodiment of the present invention.
Figure 26B:
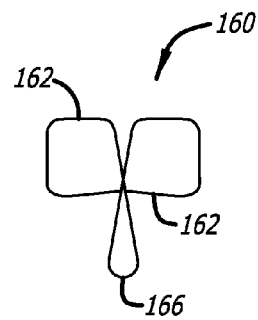
Figure 26C:
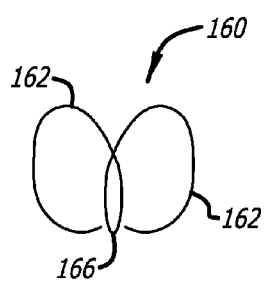
Figure 26D:
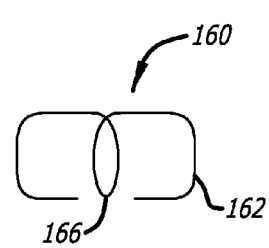

In certain of the embodiments, for example the embodiments shown in FIGS. 17, 18A and 18B, 22A and 22B, and 23, it is further contemplated that a locking or fixing of the support member 20 or the arm 26 relative to the anchor 130 is facilitated by a separate locking member 150 as shown in FIGS. 23 and 25. The locking member 150 and aperture 132' may incorporate any of the above described features for engaging the support member 20 or the arm 26. In operation, the support member 20 or the arm 26 passes through the aperture 132' of the locking member 150. The locking member 150, in turn, is configured so as to resist or be incapable of passing through the aperture 132 of the anchor 130. It is also contemplated that a suture, not shown, be attached to the locking member 150 in order to facilitate location and manipulation of the locking member during the procedure.

A method for deploying or implanting the implant 10 incorporating the anchors 130 will now be described. First, a single incision or entry point is made in the patient followed by blunt dissection as necessary or desired. One or more anchors 130 are delivered at various locations in the body using the delivery system 120 described above. Sutures that are secured to the support member 20 or the arm 26 at one end are passed through the aperture 132, 132' of the anchor 130 and used to tension the support member 20 within the body thereby setting the support member 20 in position within the body. Alternatively, the suture is omitted and the support member 20 or the arm 26 is directly passed through the aperture 132, 132' in order to set the support member 20 in position within the body. The tension of the support member 20 spanning between two corresponding anchors 132, 132' is adjusted as described above and the ends of the suture, the support member 20 or the arms 26 are secured so as to maintain the necessary tension. The ends of the suture, the support member 20 or the arm 26 are either trimmed or left in place, and the incision is closed.

Alternatively, the anchors 130 are assembled with the support member 20 prior to initiating the procedure. In such case, the step of introducing a suture, support member 10, or arm 26 through the aperture 132, 132', after the anchor 130 has been implanted is omitted. Once the anchors 130 have been implanted, the support member 20 spanning between the corresponding anchors 130 is tensioned and adjusted as described above.

Upon completion of the implantation of the implant 10, the anchor sutures 40 and support member sutures 50 can be left in place for possible use in a follow-up procedure or may be removed from the patient.

Figure 27:
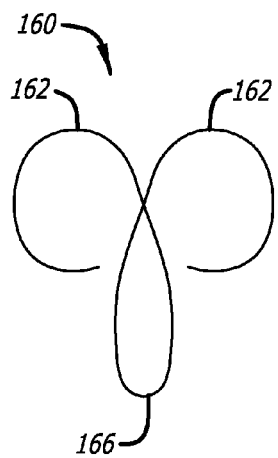
FIG. 27 is a plan view of an anchor according to an embodiment of the present invention.

FIGS. 26-30 show yet another embodiment of the present invention in which the anchors 160 take the form of a staple. As shown in FIG. 27, the anchors 160 comprises one or more retention loops 162 for piercing and engaging the target tissue and a tail loop 166 or associating the support member 20 or arm 26 with the staple 160. As shown in FIGS. 26A-26D, the shape and size of the retention loops 162 may be circular, rectangular, triangular, oval or a combination thereof. The tail loop 166 may also be formed in a variety of shapes and sizes. The tail loop 166 may, for example, be an open of closed loop and may be shaped so as to pinch a suture, the support member 20, and/or the arm 26 of the support member 20. A suture or suture loop, not shown, may further be affixed to the tail loop 166 in order to assist in assembly and implantation of the staple 160.

Figure 28A:
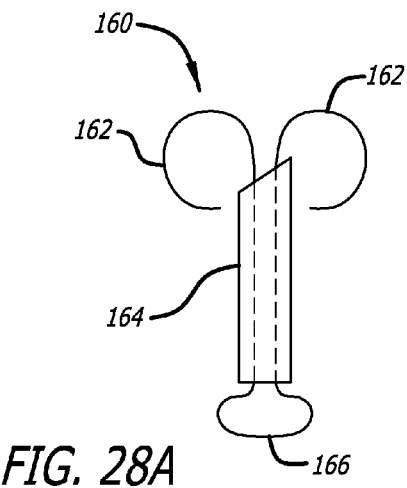
FIGS. 28A and 28B are plan views of an anchor according to an embodiment of the present invention.
Figure 28B:
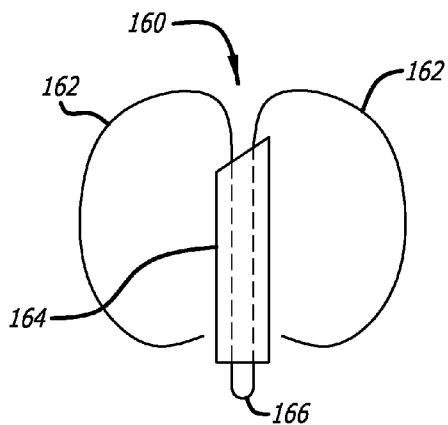
Figure 29:
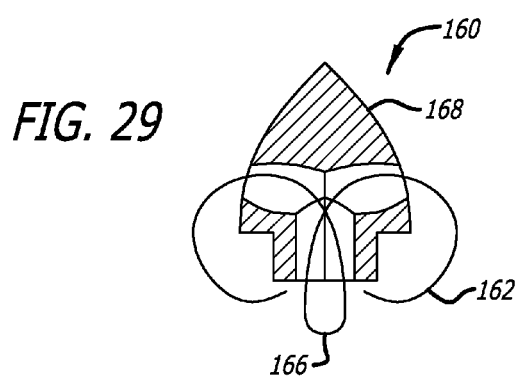
FIG. 29 is a plan view of an anchor according to an embodiment of the present invention.
Figure 30A:
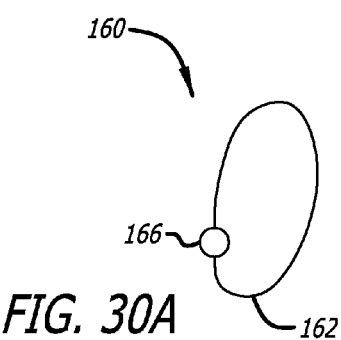
FIGS. 30A and 30B are plan views of an anchor according to an embodiment of the present invention.
Figure 30B:
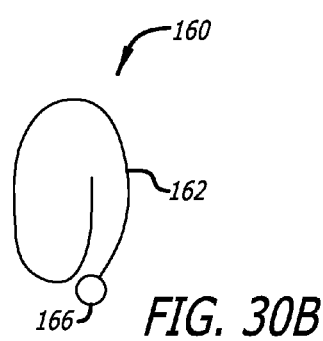

FIGS. 28A and 28B show alternative embodiments of the anchor 160 in which a portion of the tail loop 166 passes through a hollow tube 164. FIG. 29 shows another embodiment of the present invention in which the anchor 160 is incorporated into a head 168. The head 168 may initially function to pierce the target tissue and then to assist in anchoring the anchor 160 in the target tissue. FIGS. 30A and 30B show a simplified embodiment of the anchor 160 employing a singular retention loop 162 attached to a tail loop 166.

In operation, the anchor 160 is first retracted into a hollow piercing needle by pulling upon the tail loop 166 such that the anchor enters the hollow piercing needle and assumes a substantially straightened, folded configuration within the hollow piercing needle. The piercing needle is introduced into the target tissue. A pusher is inserted into an opposite end of the hollow piercing needle and used to push the anchor into the target tissue. The hollow piercing needle may, but need not be retracted from the target tissue simultaneously as the anchor 160 is pushed from out the end of the needle. As the anchor 160 exits the needle, the staple 160 penetrates in to the target tissue as it assume its unconstrained shape.

After implantation of the anchor 160 within the target tissue, the support member 20 or arm 26 is associated with the tail loop 162 by securing a suture connected to the support member 20 to the tail loop 162 or by directly securing the support member 20 or arm 26 to or through the tail loop by using any of the embodiments herein described with relation to the anchors 30 and 130.

The anchor 160 may be formed of a single or multi filament or wire fabricated from Nitinol, stainless steel or other metals, polymer or other shape memory material. The staple may be 1-30 mm tall and 1-30 mm wide.

A method for deploying or implanting the implant 10 incorporating the anchor 160 will now be described. First, a single incision or entry point is made in the patient followed by blunt dissection as necessary or desired. One or more anchor 160 are implanted at various locations within the body. Sutures that are passed through the tail loop 162 and secured to the support member 20 or the arm 26 at one end are used to tension the support member 20 within the body. Alternatively, the support member 20 or the arm 26 is directly passed through the tail loop 162 of the anchor 160 in order to set the support member 160 in position within the body. The support member 20 tension is adjusted as desired. The ends of the suture, the support member 20 or the arms 26 are secured so as to maintain the necessary tension and trimmed as desired and the incision is closed.

The implants 10 according to the present invention may employ the anchors 30, 130, or 160 exclusively or, as shown in FIGS. 1 and 2C, may employ a combination of different types of anchors. For example, FIGS. 1 and 2C shows a portion of the implant 10 that employs the anchors 30 on a first set of arms 26 and the anchors 130 on a second set of arms 26. During implantation, the anchors 30 incorporated into the first set of arms 26 are first implanted in or through the transobturator, and the anchors 130 incorporated into the second set of arms 26 are next implanted in or through the sacrospinous ligaments, SSL. It will be understood by one of skill in the art the different anchors of the present invention will each lend themselves to implantation within potentially different target tissues having different characteristics and locations within the body.

While the present invention has been described for use in treating pelvic floor disorders and incontinence, it would be understood by one of skill in the art that the present invention can be used support other organs within the body or as a means of fixation of tissue or implants within the body.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for supporting an anatomical structure comprising:
    (a) making an entry point in a body of a patient;
    (b) engaging a first anchor with a delivery system and inserting the first anchor through the entry point and into a target tissue of the body;
    (c) retracting the delivery system from the first anchor and out from the entry point;
    (d) reengaging the delivery system with the first anchor by passing a suture extending from the first anchor and out the entry point through a slot in the delivery system and advancing the delivery system towards the first anchor until the first anchor is received by the delivery system;

(e) adjusting a position of the first anchor in the target tissue with the delivery system and retracting the delivery system from the first anchor and out from the entry point after said adjusting;

(f) positioning a support member between the first anchor and a second anchor secured within said body;

(g) locking said support member in position relative to the first and second anchors by passing a mesh portion of the support member through an aperture of one of the first and second anchors and engaging said mesh portion of said support member with projections extending from an interior of the aperture by releasing a tension of a suture loop that passes through said aperture; and (h) closing said entry point.

2. The method of claim 1 wherein the step of engaging a first anchor with a delivery system and inserting the first anchor through the entry point and into a target tissue of the body comprises receiving a proximal guide protrusion of the first anchor within a distal cavity of the delivery system.

3. The method of claim 1 wherein the step of retracting the delivery system from the first anchor and out from the entry point comprises breaking a friction fit between a portion of the first anchor and a distal cavity of the delivery system.

4. The method of claim 1 wherein the step of reengaging the delivery system with the first anchor by passing a suture extending from the first anchor and out the entry point through a slot in the delivery system and advancing the delivery system towards the first anchor until the first anchor is received by the delivery system comprises receiving a proximal guide protrusion of the first anchor within a distal cavity of the delivery system.

5. The method of claim 1 wherein the step of adjusting a position of the first anchor in the target tissue with the delivery system and retracting the delivery system from the first anchor and out from the entry point after said adjusting comprises manipulating the delivery system to advance the first anchor within the target tissue.

6. The method of claim 1 wherein the aperture is circular.

7. The method of claim 1 wherein the step of positioning a support member between the first anchor and a second anchor secured within said body comprises pulling the mesh portion of said support member.

8. The method of claim 1 further comprising:
engaging the delivery system with the second anchor by passing a suture extending from the second anchor and out the entry point through the slot in the delivery system and advancing the delivery system towards the second anchor until the second anchor is received by the delivery system.

9. A method for supporting an anatomical structure comprising:

(a) making an entry point in a body of a patient;
(b) engaging a first anchor with a delivery system and inserting the first anchor through the entry point and into a target tissue of the body;
(c) retracting the delivery system from the first anchor and out from the entry point;

(d) reengaging the delivery system with the first anchor by passing a suture extending from the first anchor and out the entry point through a slot in the delivery system and advancing the delivery system towards the first anchor until the first anchor is received by the delivery system;

(e) adjusting a position of the first anchor in the target tissue with the delivery system and retracting the delivery system from the first anchor and out from the entry point after said adjusting;

(f) positioning a support member between the first anchor and a second anchor secured within said body;

(g) locking said support member in position relative to the first and second anchors by passing a mesh portion of the support member through an aperture of one of the first and second anchors, engaging said mesh portion of said support member with projections extending from an interior of the aperture, and closing a cover over the aperture; and (h) closing said entry point.

10. The method of claim 9 wherein the step of engaging a first anchor with a delivery system and inserting the first anchor through the entry point and into a target tissue of the body comprises receiving a proximal guide protrusion of the first anchor within a distal cavity of the delivery system.

11. The method of claim 9 wherein the step of retracting the delivery system from the first anchor and out from the entry point comprises breaking a friction fit between a portion of the first anchor and a distal cavity of the delivery system.

12. The method of claim 9 wherein the step of reengaging the delivery system with the first anchor by passing a suture extending from the first anchor and out the entry point through a slot in the delivery system and advancing the delivery system towards the first anchor until the first anchor is received by the delivery system comprises receiving a proximal guide protrusion of the first anchor within a distal cavity of the delivery system.

13. The method of claim 9 wherein the step of adjusting a position of the first anchor in the target tissue with the delivery system and retracting the delivery system from the first anchor and out from the entry point after said adjusting comprises manipulating the delivery system to advance the first anchor within the target tissue.

14. The method of claim 9 wherein the step of positioning a support member between the first anchor and a second anchor secured within said body comprises pulling the mesh portion of said support member.

15. The method of claim 9 further comprising:
engaging the delivery system with the second anchor by passing a suture extending from the second anchor and out the entry point through the slot in the delivery system and advancing the delivery system towards the second anchor until the second anchor is received by the delivery system.

* * * * *